US006652867B1

(12) United States Patent
Vincent et al.

(10) Patent No.: US 6,652,867 B1
(45) Date of Patent: Nov. 25, 2003

(54) COMPOSITIONS CONTAINING ORGANIC OIL-IN-WATER EMULSIONS, SALTS, ALCOHOLS AND SOLVENTS

(75) Inventors: Judith Mervane Vincent, Midland, MI (US); Yihan Liu, Midland, MI (US); Donald Taylor Liles, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 09/668,959

(22) Filed: Sep. 25, 2000

(51) Int. Cl.[7] .............................. A61K 6/00; A61K 7/00; A61K 7/32; A61K 7/06; A61K 7/11
(52) U.S. Cl. ................... 424/401; 424/65; 424/70.12; 424/78.03; 514/63; 514/938
(58) Field of Search .................. 424/401, 65, 70.1, 424/70.12, 78.03; 514/63, 715, 762, 938

(56) References Cited

U.S. PATENT DOCUMENTS

| 3,810,478 A | * | 5/1974 | Olson et al. | |
| 4,960,764 A | | 10/1990 | Figueroa, Jr. et al. | 514/63 |
| 5,216,070 A | | 6/1993 | Plochocka et al. | 524/801 |
| 5,443,760 A | | 8/1995 | Kasprzak | 424/78.03 |
| 5,449,510 A | | 9/1995 | Gregoire et al. | 424/60 |
| 5,456,906 A | * | 10/1995 | Powell et al. | 424/66 |
| 5,587,153 A | * | 12/1996 | Angelone et al. | 424/66 |
| 5,770,112 A | * | 6/1998 | Omura et al. | 252/308 |
| 5,891,954 A | | 4/1999 | Gee et al. | 524/837 |
| 5,968,495 A | * | 10/1999 | Bolich et al. | 424/70.12 |
| 5,969,038 A | | 10/1999 | Fecht et al. | 524/837 |
| 6,080,394 A | * | 6/2000 | Lin et al. | 424/78.03 |

* cited by examiner

*Primary Examiner*—Sreeni Padmanabhan
*Assistant Examiner*—Lauren Q. Wells
(74) *Attorney, Agent, or Firm*—Jim L. DeCesare

(57) ABSTRACT

Emulsions prepared using a silicone polyether as the surfactant are stable in an aqueous media in the presence of salts such as electrolytes, alcohols, solvents, and combinations thereof. The emulsions can be prepared by (i) polymerizing an unsaturated monomeric organic compound in water containing the monomer, a silicone polyether, a catalyst, and optional organic surfactants, until a polymer of desired molecular weight is obtained; (ii) by mechanically emulsifying a non-silicon atom containing organic oil in water using a silicone polyether with or without addition of other organic surfactants; and (iii) by mixing and adding a silicone polyether to a previously prepared emulsion.

23 Claims, No Drawings

COMPOSITIONS CONTAINING ORGANIC OIL-IN-WATER EMULSIONS, SALTS, ALCOHOLS AND SOLVENTS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

This invention is directed to organic oil-in-water (O/W) emulsions, and to certain compositions containing such organic O/W emulsions in combination with a salt, an alcohol, a solvent, or a combination of the salt, the alcohol, and the solvent.

BACKGROUND OF THE INVENTION

Emulsions prepared with conventional organic surfactants are generally not stable in the presence of an alcohol or a solvent. When an ionic surfactant is used, the emulsions are not stable in the presence of salts. In fact, salts, lower alkyl alcohols, and certain organic solvents, are routinely used to break emulsions into separate phases to analyze content.

However, it has been found that when a silicone polyether is used to make an organic oil-in-water emulsion or a silicone polyether is added to a previously prepared organic oil-in-water emulsion, that the organic oil-in-water emulsion is stable in the presence of a salt, an alcohol, an organic solvent, or a combination thereof. Such stability is an advantage and benefit in personal care, household care, automotive care, and coating industry applications.

U.S. Pat. No. 5,216,070 (Jun. 1, 1993) is directed to preparation of organic oil-in-water emulsions using silicone polyethers, however it arrives at the composition by a complex inversion process in which a water soluble organic monomer is dispersed in an aqueous phase. In contrast, the method according to the present invention achieves a similar result directly without inversion, and uses instead water insoluble or only partially water soluble organic monomers in an oil phase.

U.S. Pat. No. 5,443,760 (Aug. 22, 1995) is directed to oil-in-water emulsions containing silicone polyethers, but the oil phase of the oil-in-water emulsion includes silicone oils rather than only organic oils.

U.S. Pat. No. 5,891,954 (Apr. 6, 1999) is directed to silicone oil-in-water emulsions prepared with silicone polyethers which are stable in the presence of an alcohol, however the silicone polyethers are only post added to previously prepared silicone oil-in-water emulsions, and it fails to teach using only organic oils in the oil phase of oil-in-water emulsion or the stability of the emulsions in the presence of salt and solvents.

U.S. Pat. No. 5,969,038 (Oct. 19, 1999) is directed to silicone oil-in-water emulsions which are stable in the presence of a salt, but it does not use silicone polyethers, and it fails to teach using only organic oils in the oil phase of the oil-in-water emulsion, as well as the stability of the emulsions in the presence of alcohols and solvents.

BRIEF SUMMARY OF THE INVENTION

This invention relates to new compositions of matter. In particular, there are four compositions. In a first embodiment, a composition is prepared by combining a salt component and an organic O/W emulsion which contains an organic oil, a surfactant(s), and water. In a second embodiment, a composition is prepared by combining an alcohol component and the organic O/W emulsion containing the organic oil, surfactant(s), and water. In a third embodiment, a composition is prepared by combining a solvent component and the organic O/W emulsion containing the organic oil, surfactant(s), and water. In a fourth embodiment, a composition is prepared by combining the salt component, the alcohol component, the solvent component, or combinations thereof, and the organic O/W emulsion containing the organic oil, surfactant(s), and water.

These and other features of the invention will become apparent from a consideration of the detailed description.

BRIEF DESCRIPTION OF THE SEVERAL VIEWS OF THE DRAWING

Not applicable.

DETAILED DESCRIPTION OF THE INVENTION

This invention is based on the unexpected discovery that when silicone polyethers are used to prepare organic oil-in-water emulsions, the resulting formulations are stable in the presence of salts such as calcium chloride and aluminum sulfate; alcohols such as methanol, ethanol, propanol and isopropanol; and organic solvents such as pentane.

The silicone polyether can be the only emulsifier used in making these emulsion; it can be used in combination with other organic type surfactants; or it can be post added to a previously prepared emulsion. The silicone polyether can be used to make organic oil-in-water microemulsions which are also stable in the presence of such salts, alcohols, and solvents.

Silicone Polyether (SPE) Surfactant

The silicone polyether is generally water soluble or water dispersible. It can have a rake type structure wherein the polyoxyethylene or polyoxyethylene-polyoxypropylene copolymeric units are grafted onto the siloxane backbone, or the SPE can have an ABA block copolymeric structure wherein A represents the polyether portion and B the siloxane portion of an ABA structure.

Silicone polyethers suitable for use herein have the formula $MD_{0-1,000}D'_{1-100}M$, most preferably the formula $MD_{0-500}D'_{1-50}M$, where M represents monofunctional unit $R_3SiO_{1/2}$, D represents difunctional unit $R_2SiO_{2/2}$, and D' represents difunctional unit $RR'SiO_{2/2}$. In these formulas, R is an alkyl group containing 1–6 carbon atoms or an aryl group, and R' is an oxyalkylene containing moiety. The R' groups may contain only oxyethylene (EO) units; a combination of oxyethylene (EO) and oxypropylene (PO) units; or a combination of oxyethylene (EO) units, oxypropylene (PO) units, and oxybutylene (BO) units. Preferred R' groups include oxyalkylene units in the approximate ratio of $EO_{3-100}PO_{0-100}$, most preferably in the ratio $EO_{3-30}PO_{1-30}$.

R' moieties typically includes a divalent radical such as $-C_mH_{2m}-$ where m is 2–8 for connecting the oxyalkylene portion of R' to the siloxane backbone. Such moieties also contain a terminating radical for the oxyalkylene portion of R' such as hydrogen, hydroxyl, or an alkyl, aryl, alkoxy, or acetoxy group.

Silicone polyethers useful herein can also be of a type having the formula $M'D_{10-000}D'_{0-100}M'$, most preferably the formula $M'D_{10-500}D'_{0-50}M'$, wherein M' represents monofunctional unit $R_2R'SiO_{1/2}$, D represents difunctional unit $R_2SiO_{2/2}$, and D' represents difunctional unit $RR'SiO_{2/2}$. In these formulas, R can be an alkyl group containing 1–6 carbon atoms or an aryl group, and again R' represents an oxyalkylene containing moiety. As noted previously, R' groups typically contain only oxyethylene (EO) units or combinations of oxyethylene (EO) and oxypropylene (PO) units. Such R' groups include these oxyalkylene units in the ratio $EO_{3-100}PO_{0-100}$, most preferably $EO_{3-30}PO_{1-30}$.

As also noted previously, R' moieties typically include a divalent radical —$C_mH_{2m}$— where m is 2–8 for connecting the oxyalkylene portions of R' to the siloxane backbone. In addition, the moiety R' contains a terminating radical for oxyalkylene portions of R' such as hydrogen, hydroxyl, an alkyl, aryl, alkoxy, or acetoxy group.

In addition, silicone polyethers useful herein can be of a type having the formula $MD_{0-1,000}D'_{0-100}D''_{1-1,00}M$ wherein D" represents difunctional unit $RR''SiO_{2/2}$, and R" is an alkyl group containing 1–40 carbon atoms. M, D, D', and R, are the same as defined above.

Table I shows some representative silicone polyethers according to such formulas, and these compositions are referred to in the accompanying Examples.

TABLE I

| Silicone Polyether | Nominal Structure of the Silicone Polyether |
| --- | --- |
| A | $MD_{8.6}D'_{3.6}M$ where R is —$CH_3$ and R' is —$(CH_2)_3(EO)_{12}OH$ |
| B | $MD_{108}D'_{10}M$ where R is —$CH_3$ and R' is —$(CH_2)_3(EO)_{10}(PO)_4OH$ |
| C | $M'D'_{75}M'$ where R is —$CH_3$ and R' is —$(CH_2)_3(EO)_{18}(PO)_{18}OAc$ |
| D | $M'D'_{50}M'$ where R is —$CH_3$ and R' is —$(CH_2)_3(EO)_{18}(PO)_{18}OAc$ |
| E | $M'D'_{13}M'$ where R is —$CH_3$ and R' is —$(CH_2)_3(EO)_{12}OH$ |

Oil Component

For purposes of this invention, the term "organic oil" is intended to mean a non-silicon atom containing organic oil including synthetic oils and natural oils derived from animal, vegetable, or mineral sources. Representative of some suitable non-silicon atom containing organic oils which can be used are almond oil, apricot kernel oil, avocado oil, cacao butter (theobroma oil), carrot seed oil, castor oil, citrus seed oil, coconut oil, corn oil, cottonseed oil, cucumber oil, egg oil, jojoba oil, lanolin oil, linseed oil, mineral oil, mink oil, olive oil, palm oil, kernel oil, peach kernel oil, peanut oil, rapeseed oil, safflower oil, sesame oil, shark liver oil, soybean oil, sunflower seed oil, sweet almond oil, tallow (beef) oil, tallow (mutton) oil, turtle oil, vegetable oil, whale oil, and wheat germ oil; alkanes generally containing about sixteen or more carbon atoms such as hexadecane; aromatic hydrocarbons such as benzene and toluene; fluorinated hydrocarbons such as perfluorocyclohexane, perfluorohexane, perfluorododecane, and perfluoropolyethylene oxide; esters such as isopropyl laurate, isopropyl palmitate, hexyl laurate, isopropyl myristate, myristyl myristate, cetyl myristate, 2-octyldecyl myristate, isopropyl palmitate, 2-ethylhexyl palmitate, butyl stearate, decyl oleate, and 2-octyldodecyl oleate; glycol ester oils such as polypropylene glycol monooleate and neopentyl glycol 2-ethylhexanoate; and polyhydric alcohol ester oils such as isostearate triglyceride and cocofatty acid triglycerides.

Also included among the types of non-silicon atom containing organic oil which can be used herein are unsaturated monomeric organic compounds such as styrene, butyl acrylate, butadiene, vinylidene chloride, vinyl chloride, ethylene, methyl methacrylate, ethyl acrylate, vinyl acetate, methyl acrylate, and acrylonitrile; and their low molecular weight polymerization products such as polystyrene and polyethylacrylate. Most preferred, are water-insoluble monomers such as styrene, and monomers generally considered only partially water soluble.

The organic oil used in emulsions according to the invention can be a composition having a linear or branched chain, it can be saturated or unsaturated, or it can be a hydrocarbon or fluorocarbon type of organic oil. A mixture of different organic oils can also be employed.

Additional and/or Optional Organic Surfactant

While the silicone polyether is capable of functioning as the sole emulsifying agent, other optional and additional organic surfactants can be included in combination with the silicone polyether surfactant, if desired.

Such other surfactant can be a nonionic, cationic, anionic, amphoteric (zwitterionic), or a mixture of such surfactants. The nonionic surfactant should be a non-silicon atom containing nonionic emulsifier. Most preferred are alcohol ethoxylates $R2-(OCH_2CH_2)_cOH$, most particularly fatty alcohol ethoxylates. Fatty alcohol ethoxylates typically contain the characteristic group —$(OCH_2CH_2)_cOH$ which is attached to fatty hydrocarbon residue R2 which contains about eight to about twenty carbon atoms, such as lauryl ($C_{12}$), cetyl ($C_{16}$) and stearyl ($C_{18}$). While the value of "c" may range from 1 to about 100, its value is typically in the range of 2 to 40.

Some examples of suitable nonionic surfactants are polyoxyethylene (4) lauryl ether, polyoxyethylene (5) lauryl ether, polyoxyethylene (23) lauryl ether, polyoxyethylene (2) cetyl ether, polyoxyethylene (10) cetyl ether, polyoxyethylene (20) cetyl ether, polyoxyethylene (2) stearyl ether, polyoxyethylene (10) stearyl ether, polyoxyethylene (20) stearyl ether, polyoxyethylene (21) stearyl ether, polyoxyethylene (100) stearyl ether, polyoxyethylene (2) oleyl ether, and polyoxyethylene (10) oleyl ether. These and other fatty alcohol ethoxylates are commercially available under names such as ALFONIC®, ARLACEL, BRIJ, GENAPOL®, LUTENSOL, NEODOL®, RENEX, SOFTANOL, SURFONIC®, TERGITOL®, TRYCOL, and VOLPO.

Cationic surfactants useful in the invention include non-silicon atom containing compounds having quaternary ammonium hydrophilic moieties in the molecule which are positively charged, such as quaternary ammonium salts represented by $R3R4R5R6N^+X^-$ where R3 to R6 are alkyl groups containing 1–30 carbon atoms, or alkyl groups derived from tallow, coconut oil, or soy; and X is halogen such as chlorine or bromine, or X can be a methosulfate group. Most preferred are (i) dialkyldimethyl ammonium salts represented by $R7R8N^+(CH_3)_2X^-$, where R7 and R8 are alkyl groups containing 12–30 carbon atoms, or alkyl groups derived from tallow, coconut oil, or soy; and X is halogen or a methosulfate group; or (ii) monoalkyltrimethyl ammonium salts represented by R9N⁺(CH₃)₃X⁻ where R9 is an alkyl group containing 12–30 carbon atoms, or an alkyl group derived from tallow, coconut oil, or soy; and X is halogen or a methosulfate group.

Representative quaternary ammonium salts are dodecyltrimethyl ammonium bromide (DTAB), dodecyltrimethyl ammonium chloride, tetradecyltrimethyl ammonium bromide, tetradecyltrimethyl ammonium chloride, hexadecyltrimethyl ammonium bromide, hexadecyltrimethyl ammonium chloride, didodecyldimethyl ammonium bromide, dihexadecyldimethyl ammonium chloride, dihexadecyldimethyl ammonium bromide, dioctadecyldimethyl ammonium chloride, dieicosyldimethyl ammonium chloride, didocosyldimethyl ammonium chloride, dicoconutdimethyl ammonium chloride, ditallowdimethyl ammonium chloride, and ditallowdimethyl ammonium bromide. These and other quaternary ammonium salts are commercially available under names such as ADOGEN, ARQUAD, SERVAMINE, TOMAH, and VARIQUAT.

Examples of non-silicon atom containing anionic surfactants include sulfonic acids and their salt derivatives such as dodecylbenzene sulfonic acid (DBSA); alkali metal sulfosuccinates; sulfonated glyceryl esters of fatty acids such as sulfonated monoglycerides of coconut oil acids; salts of sulfonated monovalent alcohol esters such as sodium oleyl isothionate; amides of amino sulfonic acids such as the sodium salt of oleyl methyl tauride; sulfonated products of fatty acid nitriles such as palmitonitrile sulfonate; sulfonated aromatic hydrocarbons such as sodium alpha-naphthalene monosulfonate; condensation products of naphthalene sulfonic acids with formaldehyde; sodium octahydro anthracene sulfonate; alkali metal alkyl sulfates such as sodium lauryl (dodecyl) sulfate (SDS); ether sulfates having alkyl groups of eight or more carbon atoms; and alkylaryl sulfonates having one or more alkyl groups of eight or more carbon atoms.

Commercial anionic surfactants useful in this invention include triethanolamine linear alkyl sulfonate sold under the name BIO-SOFT N-300 by the Stepan Company, Northfield, Ill.; sulfates sold under the name POLYSTEP by the Stepan Company; and sodium n-hexadecyl diphenyloxide disulfonate sold under the name DOWFAX 8390 by The Dow Chemical Company, Midland, Mich.

Surfactants classified as amphoteric or zwitterionic include cocoamphocarboxy glycinate, cocoamphocarboxy propionate, cocobetaine, N-cocamidopropyldimethyl glycine, and N-lauryl-N-carboxymethyl-N-(2-hydroxyethyl)ethylene diamine. Other suitable amphoteric surfactants include the quaternary cycloimidates, betaines, and sultaines.

The betaines have the structure $R11R12R13N^+(CH_2)_n COO^-$ wherein R11 is an alkyl group having about twelve to eighteen carbon atoms or a mixture thereof, R12 and R13 are independently lower alkyl groups having one to three carbon atoms, and n is an integer from one to four. Specific betaines are α-(tetradecyldimethylammonio)acetate, β-(hexadecyldiethylammonio)propionate, and γ-(dodecyldimethylammonio)butyrate.

The sultaines have the structure $R11R12R13N^+(CH_2)_n SO_3^-$ wherein R11, R12, R13, and n are as defined above. Specific useful sultaines are 3-(dodecyldimethylammonio)-propane-1-sulfonate, and 3-(tetradecyldimethylammonio)ethane-1-sulfonate.

Representative amphoteric surfactants are products sold under the names MIRATAINE® by Rhone-Poulenc Incorporated, Cranberry, N.J.; and TEGO BETAINE by Goldschmidt Chemical Corporation, Hopewell, Va. Imidazoline and imidazoline derivatives sold under the name MIRANOL® by Rhone-Poulenc Incorporated, Cranberry, N.J. may also be employed.

Salt Component

As used herein, the term "salt" is intended to mean an inorganic salt or an organic salt, including compounds commonly referred to as electrolytes.

Some examples of suitable inorganic salts include calcium chloride, magnesium sulfate, magnesium chloride, sodium sulfate, sodium thiosulfate, sodium chloride, sodium phosphate, ammonium chloride, ammonium carbonate, iron sulfate, aluminum sulfate, aluminum chloride, aluminum chlorohydrate, aluminum sesquichlorohydrate, aluminum dichlorohydrate, aluminum zirconium tetrachorohydrex glycine, aluminum zirconium trichlorohydrate, aluminum zirconium tetrachlorohydrate, aluminum zirconium pentachlorohydrate, and aluminum zirconium octachlorohydrate.

Some examples of suitable organic salts include sodium aluminum lactate, sodium acetate, sodium dehydroacetate, sodium butoxy ethoxy acetate, sodium caprylate, sodium citrate, sodium lactate, sodium dihydroxy glycinate, sodium gluconate, sodium glutamate, sodium hydroxymethane sulfonate, sodium oxalate, sodium phenate, sodium propionate, sodium saccharin, sodium salicylate, sodium sarcosinate, sodium toluene sulfonate, magnesium aspartate, calcium propionate, calcium saccharin, calcium d-saccharate, calcium thioglycolate, aluminum caprylate, aluminum citrate, aluminum diacetate, aluminum glycinate, aluminum lactate, aluminum methionate, aluminum phenosulfonate, potassium aspartate, potassium biphthalate, potassium bitartrate, potassium glycosulfate, potassium sorbate, potassium thioglycolate, potassium toluene sulfonate, and magnesium lactate.

Alcohol Component

The term "alcohol" as used herein is intended to mean a lower alkyl alcohol such as ethanol. Examples of some other appropriate lower alkyl alcohols which can be used are methyl alcohol, propyl alcohol, isopropyl alcohol, butyl alcohol, and isobutyl alcohol. Generally, these lower alkyl alcohols will contain one to about four carbon atoms.

Solvent Component

Solvents which can be used herein include alkanes with generally less than about 16 carbon atoms such as pentane and hexane; ketones such as acetone, methyl ethyl ketone, methyl n-butyl ketone, and methyl amyl ketone; aromatic compounds such as benzene, toluene, and ethylbenzene; esters such as ethyl acetate, isopropyl acetate, methyl acetoacetate, and isobutyl isobutyrate; ethers such as ethyl ether, butyl ethyl ether, isopentyl ether, propylene oxide, and tetrahydrofuran; glycols such as ethylene glycol, propylene glycol, and diethylene glycol; and chlorinated hydrocarbons such as methylene chloride, chloroform, carbon tetrachloride, ethyl chloride, and chlorobenzene.

Emulsion Preparation

The mechanical preparation of an emulsion involves mixing water, one or more surfactants, and an oil, and homogenizing the mixture using a laboratory homogenizer or other device for applying vigorous agitation. The silicone polyether can be incorporated in the mechanical process as the sole emulsifier, or it can be used with a co-surfactant such as another organic surfactant. Alternatively, the silicone polyether can be post-added to a previously prepared emulsion.

The process of preparing emulsions by the emulsion polymerization process involve mixing water, surfactant(s), and oil monomers, with a polymerization catalyst. The mixture is agitated until essentially all of the oil monomer is reacted and consumed, and a stable emulsion or microemulsion is formed. The silicone polyether is preferably incorporated before polymerization occurs, i.e., before the catalyst is added. The post addition of the silicone polyether to emulsions prepared by emulsion polymerization has been found to be less effective in providing salt, alcohol, and solvent stability.

In particular, this method of making such organic oil-in-water emulsions involves (i) preparing an aqueous phase containing water, a silicone polyether surfactant, and optionally one or more organic surfactants; (ii) preparing an oil phase comprising a non-silicon atom containing unsaturated organic monomer; (iii) combining the aqueous phase and the oil phase, and applying shear; (iv) adding a polymerization catalyst to the combined phase; (v) agitating the combined phase for a time sufficient to allow the non-silicon atom containing unsaturated organic monomer to polymerize to an organic polymer of the desired molecular weight; and (vi) recovering the organic oil-in-water emulsion containing the organic polymer in the oil phase of the organic oil-in-water emulsion.

Such emulsions, whether prepared mechanically or by emulsion polymerization, typically have their pH adjusted to 6–7.5, and in general contain 5–80 percent by weight of oil, preferably 20–60 percent; 0.1–20 percent by weight of the surfactant(s), preferably 0.1–10 percent; and 20–90 percent by weight of water, based on the weight of the emulsion.

Optional Components

Since emulsions are susceptible to microbiological contamination, a preservative may be required as an optional component of the emulsion, and some representative compounds which can be used include formaldehyde, salicylic acid, phenoxyethanol, DMDM hydantoin (1,3-dimethylol-5,5-dimethyl hydantoin), 5-bromo-5-nitro-1,3-dioxane, methyl paraben, propyl paraben, sorbic acid, imidazolidinyl urea sold under the name GERMALL® 11 by Sutton Laboratories, Chatham, N.J., sodium benzoate, 5-chloro-2-methyl-4-isothiazolin-3-one sold under the name KATHON CG by Rohm & Haas Company, Philadelphia, Pa., and iodopropynl butyl carbamate sold under the name GLYCACIL® L by Lonza Incorporated, Fair Lawn, N.J.

A freeze/thaw stabilizer can be included as an optional component of the emulsion including compounds such as ethylene glycol, propylene glycol, glycerol, trimethylene glycol, and polyoxyethylene ether alcohols such as products sold under the name RENEX 30 by ICI Surfactants, Wilmington, Del.

Another optional component of the emulsion which can be included is a corrosion inhibitor such as an alkanolamine, an inorganic phosphate such as zinc dithiophosphate, an inorganic phosphonate, an inorganic nitrite such as sodium nitrite, a silicate, a siliconate, an alkyl phosphate amine, a succinic anhydride such as dodecenyl succinic anhydride, an amine succinate, or an alkaline earth sulfonate such as sodium sulfonate or calcium sulfonate.

Compositions

A first composition which can be prepared according to the concept of the present invention contains:
(i) 1–30 percent by weight of the salt component, and
(ii) 70–99 percent by weight of the organic O/W emulsion, which as noted above, contains 5–80 percent by weight of the organic oil, 0.1–20 percent by weight of the surfactant(s), and 20–90 percent by weight of water. This first composition is in the form of an O/W emulsion.

A second composition which can be prepared according to the concept of the present invention contains:
(i) 1–80 percent by weight of the alcohol component, and
(ii) 20–99 percent by weight of the organic O/W emulsion, which as noted above, contains 5–80 percent by weight of the organic oil, 0.1–20 percent by weight of the surfactant(s), and 20–90 percent by weight of water. This second composition is in the form of an O/W emulsion.

A third composition which can be prepared according to the concept of the present invention contains:
(i) 1–99 percent by weight of the solvent component, and
(ii) 1–99 percent by weight of the organic O/W emulsion, which as noted above, contains 5–80 percent by weight of the organic oil, 0.1–20 percent by weight of the surfactant(s), and 20–90 percent by weight of water. This third composition is in the form of a two-phase system wherein one phase contains the solvent and the other phase contains the stable O/W emulsion; or it can be in the form of a homogeneous single phase containing the solvent and the stable O/W emulsion.

A fourth composition which can be prepared according to the concept of the present invention contains:
i) 1–30 percent by weight of the salt component,
(ii) 10–80 percent by weight of the alcohol component,
(iii) 1–80 percent by weight of the solvent component, and
(iv) 10–90 percent by weight of the organic O/W emulsion, which as noted above, contains 5–80 percent by weight of the organic oil, 0.1–20 percent by weight of the surfactant(s), and 20–90 percent by weight of water. This fourth composition is in the form of an emulsion.

When it is desired to include an optional component in these compositions, 0.01–0.1 percent by weight of each optional component, i.e., preservative, freeze/thaw stabilizer, or corrosion inhibitor, can be added to the composition.

Such compositions can generally be prepared at room temperature using simple propeller mixers, turbine-type mixers, Brookfield counter-rotating mixers, or homogenizing mixers. No special equipment or processing conditions are generally required.

Stability Measure

Emulsion stability was evaluated by visual observation. Emulsion instability was determined as being indicated by the emulsion separating into an oil-rich and a water-rich layer or sedimentation. Only the initial stability was determined in the examples. However, many of the formulations showed long term stability of the order of weeks and months.

EXAMPLES

The following examples are set forth in order to illustrate this invention in more detail.

Example I

In a cream jar was added 45.95 g of water, 1 g of sodium dodecyl sulfate (SDS) as an anionic surfactant, and 30 g of hexadecane. The mixture was sonicated with a soniprobe until it was homogenous. The emulsion which formed is hereafter referred to as Emulsion I. Emulsion I was further diluted by adding an equal amount of water and mixing for 5 hours. A final emulsion was formed and it is hereafter referred to as Emulsion Ia. Emulsion Ia was tested for stability in the presence of salts, alcohols, and a solvent, and the results are shown below.

| Emulsion Ia | $CaCl_2$ | MeOH | EtOH | IPA | Pentane | Stability Observed |
|---|---|---|---|---|---|---|
| 5 g | 0.9 g | | | | | Unstable, irreversible phase separation |
| 5 g | | 15 ml | | | | Flocculated, redispersible by shaking |
| 5 g | | | 15 ml | | | Flocculated, redispersible by shaking |
| 5 g | | | | 15 ml | | Flocculated, redispersible by shaking |
| 5 g | | | | | 15 ml | Emulsion intact at bottom in methanol |
| 5 g | 0.25 g | 12.5 ml | | | 12.5 ml | Unstable, irreversible phase separation |

To 15 g of Emulsion I was added 10 g water and 4 g of SPE D of the structure shown in Table I, and it was mixed for 24 hours. A final emulsion was formed and is hereafter referred to as Emulsion Ib. Emulsion Ib was tested for stability, and the results are shown below.

| Emulsion Ib | $CaCl_2$ | MeOH | EtOH | IPA | Pentane | Stability Observed |
|---|---|---|---|---|---|---|
| 5 g | 0.25g | | | | | Stable |
| 5 g | | 15 ml | | | | Stable |
| 5 g | | | 15 ml | | | Stable |
| 5 g | | | | 15 ml | | Stable |
| 5 g | | | | | 15 ml | Emulsion intact at bottom |
| 5 g | 0.25g | 12.5 ml | | | 12.5 ml | Forms homogenous single phase |

Example II

In a cream jar was added 15 g water, 10 g of SPE D of the structure shown in Table I, and 25 g hexadecane. The mixture was sonicated with a soniprobe until it was homogenous, and then it was agitated for another 15 hours with a magnetic stirrer. The emulsion which formed is hereafter referred to as Emulsion II. Emulsion II was tested for stability and the results are shown below.

| Emulsion II | $CaCl_2$ | MeOH | EtOH | IPA | Pentane | Stability Observed |
|---|---|---|---|---|---|---|
| 5 g | 0.9 g in 15 g $H_2O$ | | | | | Stable |
| 5 g | | 15 ml | | | | Stable |
| 5 g | | | 15 ml | | | Stable |
| 5 g | | | | 15 ml | | Stable |
| 5 g | 0.25 g | 12.5 ml | | | 12.5 ml | Stable, forms homogeneous one phase emulsion |

Example III

Oil Phase A was formed by mixing together 25 g of mineral oil, 4 g of Arlacel 165 nonionic surfactant, and 2 g of stearyl alcohol as nonionic surfactant. Aqueous Phase A was mixed and heated at 80° C. Phase B was formed by mixing together 5 g of glycerol as a freeze/thaw additive and 64 g of water. Phase B was also mixed and heated at 80° C. Phase A was added to Phase B. The mixture of Phases A and B was cooled to room temperature. The emulsion which was formed is hereafter referred to as Emulsion IIIa. Emulsion IIIa was tested for stability and the results are shown below. Arlacel 165 is the name of a product sold by ICI Surfactants, Wilmington Del. Arlacel 165 nonionic surfactant consists of a mixture of glycerol monostearate and polyoxyethylene stearate.

| Emulsion IIIa | $CaCl_2$ | $Al_2(SO_4)_3$ | MeOH | EtOH | Pentane | Stability Observed |
|---|---|---|---|---|---|---|
| 5g | | 1 g | | | | Flocculated, redispersible by shaking |
| 5g | | | | 15 ml | | Unstable, irreversible agglomeration |
| 5g | 0.25 g | | 12.5 ml | | 12.5 ml | Unstable, oil extracted |

In a cream jar was added 28.5 g of Emulsion IIIa and 1.5 g of SPE E of the structure shown in Table I. The mixture was sonicated with a soniprobe and then stirred for 5 minutes. The emulsion which was formed is hereafter referred to as Emulsion IIIb. Emulsion IIIb was tested for stability and the results are shown below.

| Emulsion IIIb | CaCl$_2$ | Al$_2$(SO$_4$)$_3$ | MeOH | EtOH | IPA | Pentane | Stability Observed |
|---|---|---|---|---|---|---|---|
| 5 g | | 1 g | | | | | Stable |
| 5 g | | | 15 ml | | | | Stable |
| 5 g | | | | 15 ml | | | Flocculated, redispersible by shaking |
| 5 g | | | | | 15 ml | | Flocculated, redispersible by shaking |
| 5 g | 0.25 g | | 12.5 ml | | | 12.5 ml | Flocculated, redispersible by shaking |

To 40 g of Emulsion IIIa was added 4 g of SPE B of the structure shown in Table I. The mixture was agitated with a laboratory mixer for 15 hours. The emulsion which was formed is hereafter referred to as Emulsion IIIc. Emulsion IIIc was tested for stability and the results are shown below.

| Emulsion IIIc | CaCl$_2$ | Al$_2$(SO$_4$)$_3$ | MeOH | EtOH | IPA | Pentane | Stability Observed |
|---|---|---|---|---|---|---|---|
| 5 g | | 1 g | | | | | stable |
| 5 g | | | 15 ml | | | | Flocculated, redispersible by shaking |
| 5 g | | | | 15 ml | | | Flocculated, redispersible by shaking |
| 5 g | | | | | 15 ml | | Flocculated, redispersible by shaking |
| 5 g | 0.25 g | | 12.5 ml | | | 12.5 ml | Emulsion remains intact in bottom layer of methanol |

Example IV

In this example, a polyethylacrylate-in-water emulsion was prepared by emulsion polymerization. To a round bottom flask was added 131.88 g of water and 7 g of SDS. This mixture was stirred at 250 RPM until dispersed. To the mixture was added 50 g of ethyl acrylate monomer, and it was mixed for at least 5 minutes. A three part catalyst package consisting of a 5 percent aqueous solution of potassium persulfate, a 5 percent aqueous solution of sodium metabisulfate, and a one percent aqueous solution of iron (II) sulfate heptahydrate, was then prepared. To the mixture was added 6.94 g of the persulfate solution. Thirty seconds later, 3.48 g of the metabisulfate solution was added. After another thirty seconds, 0.70 g of the iron sulfate solution was added. The temperature in the flask increased immediately. The reaction was completed after the temperature had plateaued. For polymerizing the ethyl acrylate monomer, this occurred within about thirty minutes. The components used in this example in terms of percent by weight were 65.94 percent of water, 3.5 percent of SDS, 25 percent of ethyl acrylate, 3.47 percent of the potassium persulfate initiator, 1.74 percent of the sodium metabisulfite redox coupling agent, and 0.35 percent of the ferrous sulfate redox coupling agent.

The emulsion which was formed is hereafter referred to as Emulsion IV. Emulsion IV was tested for stability and the results are shown below.

| Emulsion IV | CaCl$_2$ | Al$_2$(SO$_4$)$_3$ | MeOH | EtOH | IPA | Pentane | Stability Observed |
|---|---|---|---|---|---|---|---|
| 5 g | 0.25 g | | | | | | Unstable, polymer precipitated |
| 5 g | | 1 g | | | | | Unstable, polymer precipitated |
| 5 g | | | 15 ml | | | | Unstable, polymer precipitated |
| 5 g | | | | 15 ml | | | Unstable, polymer precipitated |
| 5 g | | | | | 15 ml | | Unstable, polymer precipitated |
| 5 g | | | | | | 15 ml | Unstable, polymer extracted by pentane |
| 5 g | 0.25 g | | 12.5 ml | | | 12.5 ml | Unstable, polymer precipitated |

Example V

A polyethylacrylate-in-water emulsion was prepared by substituting 3.0 percent of SPE A of the structure shown in Table I for the 3.5 percent of the SDS in Example IV. The amount of water was adjusted for balance. The emulsion which was formed is hereafter referred to as Emulsion V. Emulsion V was tested for stability and the results are shown below.

| Emulsion V | CaCl$_2$ | Al$_2$(SO$_4$)$_3$ | MeOH | EtOH | IPA | Pentane | Stability Observed |
|---|---|---|---|---|---|---|---|
| 5 g | 0.25 g | | | | | | Stable |
| 5 g | | 1 g in 15 g H$_2$O | | | | | Stable |
| 5 g | | | 15 ml | | | | Unstable, polymer precipitated |
| 5 g | | | | 15 ml | | | Stable, forms clear emulsion |
| 5 g | | | | | 15 ml | | Stable, forms clear emulsion |
| 5 g | | | | | | 15 ml | Emulsion remains intact at bottom |
| 5 g | 0.25 g | | 12.5 ml | | | 12.5 ml | Unstable, polymer precipitated |

Example VI

Styrene monomer was substituted for the ethyl acrylate monomer in Example V, and a polystyrene-in-water emulsion was prepared. The emulsion which was formed is hereafter referred to as Emulsion VI. Emulsion VI was tested for stability and the results are shown below.

| Emulsion VI | CaCl$_2$ | Al$_2$(SO$_4$)$_3$ | MeOH | EtOH | IPA | Pentane | Stability Observed |
|---|---|---|---|---|---|---|---|
| 5 g | 0.25 g | | | | | | Stable |
| 5 g | | 1 g in 10 g H$_2$O | | | | | Stable |
| 5 g | | | 15 ml | | | | Stable |
| 5 g | | | | 15 ml | | | Stable |
| 5 g | | | | | 15 ml | | Stable |
| 5 g | | | | | | 15 ml | Emulsion remains intact at bottom |
| 5 g | 0.25 g | | 12.5 ml | | | 12.5 ml | Unstable, polymer precipitated |

Example VII

Example V was repeated except that 15.0 percent of SPE C of the structure shown in Table I was substituted for the 3.0 percent of SPE A of the structure shown in Table I. The amount of water was adjusted for balance. The emulsion which was formed is hereafter referred to as Emulsion VII. Emulsion VII was tested for stability and the results are shown below.

| Emulsion VII | CaCl$_2$ | Al$_2$(SO$_4$)$_3$ | MeOH | EtOH | IPA | Pentane | Stability Observed |
|---|---|---|---|---|---|---|---|
| 5 g | 0.25 g | | | | | | Unstable, polymer precipitated |
| 5 g | | 1 g | | | | | Unstable, polymer precipitated |
| 5 g | | | 15 ml | | | | Unstable, polymer precipitated |
| 5 g | | | | 15 ml | | | Stable |
| 5 g | | | | | 15 ml | | Stable |
| 5 g | | | | | | 15 ml | Emulsion remains intact at bottom |
| 5 g | 0.25 g | | 12.5 ml | | | 12.5 ml | Unstable |

Emulsions prepared according to this invention are useful in paper coating, textile coating, personal care, household care, automotive care, and petroleum industry, applications for delivering silicone polymers to various surfaces and substrates. For example, in personal care, they can be used in underarm products such as antiperspirants and deodorants, hair care products such as styling aids, and in products used in the care of skin.

Other variations may be made in compounds, compositions, and methods described herein without departing from the essential features of the invention. The embodiments of the invention specifically illustrated herein are exemplary only and not intended as limitations on their scope except as defined in the appended claims.

What is claimed is:

1. A composition comprising (i) 1–30 percent by weight of a salt component, and (ii) 70–99 percent by weight of an organic oil-in-water emulsion; the organic oil-in-water emulsion comprising 5–80 percent by weight of a non-silicon atom containing organic oil, 0.1–20 percent by weight of a silicone polyether surfactant, and 20–90 percent by weight of water.

2. A composition according to claim 1 in which the salt component is an inorganic salt or an organic salt selected from the group consisting of calcium chloride, magnesium sulfate, magnesium chloride, sodium sulfate, sodium thiosulfate, sodium chloride, sodium phosphate, ammonium chloride, ammonium carbonate, iron sulfate, aluminum sulfate, aluminum chloride, aluminum chlorohydrate, aluminum sesquichlorohydrate, aluminum dichlorohydrate, aluminum zirconium tetrachorohydrex glycine, aluminum zirconium trichlorohydrate, aluminum zirconium tetrachlorohydrate, aluminum zirconium pentachlorohydrate, aluminum zirconium octachlorohydrate, sodium aluminum lactate, sodium acetate, sodium dehydroacetate, sodium butoxy ethoxy acetate, sodium caprylate, sodium citrate, sodium lactate, sodium dihydroxy glycinate, sodium gluconate, sodium glutamate, sodium hydroxymethane sulfonate, sodium oxalate, sodium phenate, sodium propionate, sodium saccharin, sodium salicylate, sodium sarcosinate, sodium toluene sulfonate, magnesium aspartate, calcium propionate, calcium saccharin, calcium d-saccharate, calcium thioglycolate, aluminum caprylate, aluminum citrate, aluminum diacetate, aluminum glycinate, aluminum lactate, aluminum methionate, aluminum phenosulfonate, potassium aspartate, potassium biphthalate, potassium bitartrate, potassium glycosulfate, potassium sorbate, potassium thioglycolate, potassium toluene sulfonate, and magnesium lactate.

3. A product containing the composition according to claim 1, the product being selected from the group consisting of coating products, personal care products, household care products, automotive care products, and petroleum products.

4. A method of treating the underarm, hair, or skin, of the human body comprising applying to the underarm, hair, or skin of the human body the personal care product according to claim 3.

5. A composition comprising (i) 1–80 percent by weight of an alcohol component, and (ii) 20–99 percent by weight of an organic oil-in-water emulsion; the organic oil-in-water emulsion comprising 5–80 percent by weight of a non-silicon atom containing organic oil, 0.1–20 percent by weight of a silicone polyether surfactant, and 20–90 percent by weight of water.

6. A composition according to claim 5 in which the alcohol component is a lower alkyl alcohols containing one to about four carbon atoms.

7. A product containing the composition according to claim 5, the product being selected from the group consisting of coating products, personal care products, household care products, automotive care products, and petroleum products.

8. A method of treating the underarm, hair, or skin, of the human body comprising applying to the underarm, hair, or skin of the human body the personal care product according to claim 7.

9. A composition comprising (i) 1–99 percent by weight of a solvent component, and (ii) 1–99 percent by weight of an organic oil-in-water emulsion; the organic oil-in-water emulsion comprising 5–80 percent by weight of a non-silicon atom containing organic oil, 0.1–20 percent by weight of a silicone polyether surfactant, and 20–90 percent by weight of water.

10. A composition according to claim 9 in which the solvent component is an alkane containing less than about 16 carbon atoms, a ketone, an aromatic compound, an ester, an ether, a glycol, or a chlorinated hydrocarbon.

11. A product containing the composition according to claim 9, the product being selected from the group consisting of coating products, personal care products, household care products, automotive care products, and petroleum products.

12. A method of treating the underarm, hair, or skin, of the human body comprising applying to the underarm, hair, or skin of the human body the personal care product according to claim 11.

13. A composition comprising (i) 1–30 percent by weight of a salt component, (ii) 10–80 percent by weight of an alcohol component, (iii) 1–80 percent by weight of a solvent component, and (iv) 10–90 percent by weight of an organic oil-in-water emulsion; the organic oil-in-water emulsion comprising 5–80 percent by weight of a non-silicon atom containing organic oil, 0 1–20 percent by weight of a silicone polyether surfactant, and 20–90 percent by weight of water.

14. A composition according to claim 13 in which the salt component is an inorganic salt or an organic salt selected from the group consisting of calcium chloride, magnesium sulfate, magnesium chloride, sodium sulfate, sodium thiosulfate, sodium chloride, sodium phosphate, ammonium chloride, ammonium carbonate, iron sulfate, aluminum sulfate, aluminum chloride, aluminum chlorohydrate, aluminum sesquichlorohydrate, aluminum dichlorohydrate, aluminum zirconium tetrachorohydrex glycine, aluminum zirconium trichlorohydrate, aluminum zirconium tetrachlorohydrate, aluminum zirconium pentachlorohydrate, aluminum zirconium octachlorohydrate, sodium aluminum lactate, sodium acetate, sodium dehydroacetate, sodium butoxy ethoxy acetate, sodium caprylate, sodium citrate, sodium lactate, sodium dihydroxy glycinate, sodium gluconate, sodium glutamate, sodium hydroxymethane sulfonate, sodium oxalate, sodium phenate, sodium propionate, sodium saccharin, sodium salicylate, sodium sarcosinate, sodium toluene sulfonate, magnesium aspartate, calcium propionate, calcium saccharin, calcium d-saccharate, calcium thioglycolate, aluminum caprylate, aluminum citrate, aluminum diacetate, aluminum glycinate, aluminum lactate, aluminum methionate, aluminum phenosulfonate, potassium aspartate, potassium biphthalate, potassium bitartrate, potassium glycosulfate, potassium sorbate, potassium thioglycolate, potassium toluene sulfonate, and magnesium lactate.

15. A composition according to claim 13 in which the alcohol component is a lower alkyl alcohol containing one to about four carbon atoms.

16. A composition according to claim 13 in which the solvent component is an alkane containing less than about 16 carbon atoms, a ketone, an aromatic compound, an ester, an ether, a glycol, or a chlorinated hydrocarbon.

17. A product containing the composition according to claim 13, the product being selected from the group consisting of coating products, personal care products, household care products, automotive care products, and petroleum products.

18. A method of treating the underarm, hair, or skin, of the human body comprising applying to the underarm, hair, or skin of the human body the personal care product according to claim 17.

19. A method of making an organic oil-in-water emulsion comprising (i) preparing an aqueous phase containing water, a silicone polyether surfactant, and optionally one or more organic surfactants; (ii) preparing an oil phase comprising a non-silicon atom containing unsaturated organic monomer; (iii) combining the aqueous phase and the oil phase ; (iv) adding a polymerization catalyst to the combined phase; (v)

agitating the combined phase for a time sufficient to allow the non-silicon atom containing unsaturated organic monomer to polymerize; and (vi) recovering an organic oil-in-water emulsion containing an organic polymer in the oil phase of the organic oil-in-water emulsion.

20. A method according to claim 19 in which the unsaturated organic monomer is selected from the group consisting of styrene, butyl acrylate, butadiene, vinylidene chloride, vinyl chloride, ethylene, methyl methacrylate, ethyl acrylate, vinyl acetate, methyl acrylate, and acrylonitrile.

21. An organic oil-in-water emulsion prepared by the method according to claim 19.

22. A product containing the organic oil-in-water emulsion according to claim 21, the product being selected from the group consisting of coating products, personal care products, household care products, automotive care products, and petroleum products.

23. A method of treating the underarm, hair, or skin, of the human body comprising applying to the underarm, hair, or skin of the human body the personal care product according to claim 22.

* * * * *